United States Patent
Yang et al.

(10) Patent No.: US 6,699,901 B1
(45) Date of Patent: Mar. 2, 2004

(54) DICARBOXYLATO DIAMMINE PLATINUM DERIVATIVES AND COMPOSITIONS COMPRISING THEM AS ANTI-TUMOR AGENTS

(76) Inventors: Xuqing Yang, No. 3023-25, Room of Chemical Building, Chemistry Department of Peking University, 100871 Beijing (CN); Zhenyun Yang, No. 3023-25, Room of Chemical Building, Chemistry Department of Peking University, 100871 Beijing (CN); Yingwu Yin, No. 3023-25, Room of Chemical Building, Chemistry Department of Peking University, 100871 Beijing (CN); Weichuan Cui, No. 3023-25, Room of Chemical Building, Chemistry Department of Peking University, 100871 Beijing (CN); Jinli Yang, No. 3023-25, Room of Chemical Building, Chemistry Department of Peking University, 100871 Beijing (CN); Chenxia Zhu, No. 3023-25, Room of Chemical Building, Chemistry Department of Peiking University, 100871 Beijing (CN)

( * ) Notice: Subject to any disclaimer, the term of this patent is extended or adjusted under 35 U.S.C. 154(b) by 0 days.

(21) Appl. No.: 10/019,150

(22) PCT Filed: Sep. 26, 2000

(86) PCT No.: PCT/CN00/00290

§ 371 (c)(1),
(2), (4) Date: Aug. 12, 2000

(87) PCT Pub. No.: WO01/64696

PCT Pub. Date: Sep. 7, 2001

(30) Foreign Application Priority Data

Mar. 3, 2000 (CN) ............................... 00 1 03393
Sep. 20, 2000 (CN) ............................... 00 1 24864 A

(51) Int. Cl.$^7$ .......................... A61K 31/28; C07F 15/00
(52) U.S. Cl. ........................................ 514/492; 556/137
(58) Field of Search .......................... 556/137; 514/492

(56) References Cited

U.S. PATENT DOCUMENTS 4,657,927 A    4/1987   Cleare et al. ............... 514/492

FOREIGN PATENT DOCUMENTS

| EP | 0 181 166 A2 | 5/1986 | .......... A61K/33/24 |
|----|--------------|--------|----------------------|
| EP | 0 275 559 A1 | 7/1988 | .......... C07F/15/00 |
| EP | 0 282 672 A1 | 9/1988 | .......... C07F/15/00 |
| EP | 0 642 792 A1 | 3/1995 | .......... A61K/31/28 |
| JP | 8-20594 | 1/1996 | .......... C07F/15/00 |
| WO | WO 95/20956 | 8/1995 | .......... A61K/31/28 |

*Primary Examiner*—Porfirio Nazario-Gonzalez
(74) *Attorney, Agent, or Firm*—Fish & Richardson P.C.

(57) ABSTRACT

The present invention relates to an antitumor derivative of double dicarboxylic acid diaminoplatin complex of formula (I):

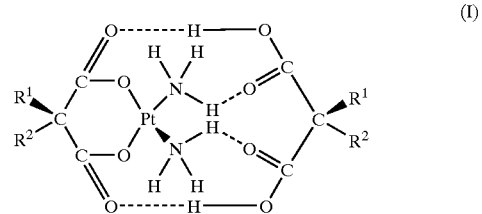

wherein $R^1$ and $R^2$ have the meanings defined in the specification, also relates to a process for preparation thereof, to an antitumor pharmaceutical composition containing the same, and further to application of the derivative in making antitumor pharmaceutics. The composition is a new generation of safe and effective antitumor drug, which has advantages such as low toxicity, broad antitumor spectrum, high antitumor activity, good solubility in water and fine stability in aqueous solution, selective killing of cancer cells without damaging normal cells, etc.

11 Claims, 11 Drawing Sheets

DICARBOXYLATO DIAMMINE PLATINUM DERIVATIVES AND COMPOSITIONS COMPRISING THEM AS ANTI-TUMOR AGENTS

The invention relates to novel kind of antitumor platin derivatives, more specifically to a derivative of double dicarboxylic acid diaminoplatin complex. The invention also relates to a process for preparation thereof, and to a pharmaceutical composition containing the same. Furthermore, the invention relates to application of the derivative in preparing antitumor pharmaceutics.

Since B. Rosenber found an antitumor effect of cis-dichlorodiaminoplatin in 1969, cisplatin has been used widely in clinical medicine as an antitumor drug of platin analogues. Though this kind of drug has obvious therapeutic effects to many cancers such as genitourinary cancer, nasopharyngeal cancer, cephalocircular cancer and lung cancer, it has high toxicity and severe side effects. Some undesirable effects such as nephrotoxicity, neurotoxcity, ototoxicity, nausea, vomitting are all constraints to its dosage and long term use. Carboplatin, one of the second-generation antitumor drugs of platin analogues, has a antitumor spectrum similar to cisplatin and has a cross drug-resistance. The therapeutical effect of carboplatin is a little inferior to that of cisplatin. Though the toxicity and side effects of carboplatin is significantly less than that of cisplatin, there still exists myelosuppression, and moreover it is not stable in aqueous solution. Therefore, active studies in search of antitumor pharmaceutics of platin analogues with high effect, low toxicity and broad-spectrum have had been made.

It is reported that many kinds of new antitumor drugs of platin analogues have entered into clinical trials in recent years, such as isoplatin, oxaliplatin, ormajplatin, lobaplatin, enloplatin, zeninplatin, L-NDOP, DWA-2114A and CI-973 etc. Though most of these new platin analogues have no cross drug-resistance with cisplatin, their antitumor strains are nearly identical to those of cisplatin, yet the antitumor spectrum is not broader and the stability in water is comparatively poor. As to toxicity, most of them are lower than that of cisplatin, some still display obvious nephrotoxicity, neurotoxicity and myelosuppression. For these reasons, none of them has been used clinically. As for the orally effective antitumor drugs of platin analogues, none has been reported up to now. It is desired that another kind of antitumor drugs of platin analogues with more effect, less toxicity and more stability in water.

After deep and thorough studying of platin analogous compounds, the inventor found surprisingly that derivatives of double dicarboxylic acid diaminoplatin complex could overcome the above-mentioned shortcomings, and have high effect, low toxicity and stability in water, thereby the present invention is effected.

The primary object of the invention is to provide a novel antitumor derivative of double dicarboxylic acid diaminoplatin complex that overcomes the shortcomings of the above-mentioned prior art.

Another object of the invention is to provide a process for preparing the derivative of double dicarboxylic acid diaminoplatin complex.

Still another object of the invention is to provide an antitumor pharmaceutical composition containing the derivative of double dicarboxylic acid diaminoplatin complex as active component.

A further object of the invention is to provide an application of the derivative of double dicarboxylic acid diaminoplatin complex in preparing antitumor pharmaceutics.

The invention relates to an antitumor derivative of double dicarboxylic acid diaminoplatin complex, characterized in that, it has following formula (I):

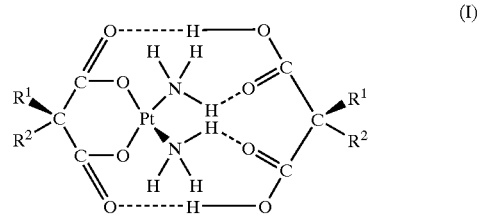

where
$R^1$ and $R^2$ are same or different, and independently represent hydrogen, a $C_1$–$C_{12}$-alkyl group, halogen, an amino group, a cyanide group, a hydroxyl group, an acyl group, a phosphoryl group or a phosphoamido group;
or represent a saturated or unsaturated 3–12-element carbocycle, which is formed by interlinking $R^1$ and $R^2$ together with the carbon atoms that $R^1$ and $R^2$ are attached to.

Preferably a saturated 3–6-element carbocycle is formed by interlinking $R^1$, $R^2$ and the carbon atoms attached to them.

More preferably, the derivative of double dicarboxylic acid diaminoplatin complex is double 1,1-cyclopropane dicarboxylic acid diaminoplatin complex or double 1,1-cyclobutane dicarboxylic acid diaminoplatin complex.

Most preferably, the derivative of present invention is double 1,1-cyclobutane dicarboxylic acid diaminoplatin complex ( ) of formula (II):

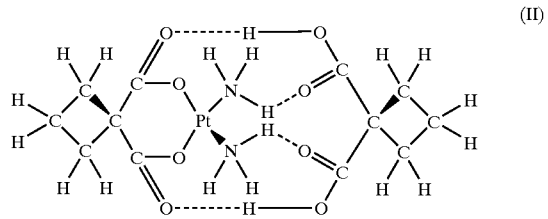

The invention also relates a process for preparing derivative of double dicarboxylic acid diaminoplatin complex, characterized in that, said derivative has following formula (I):

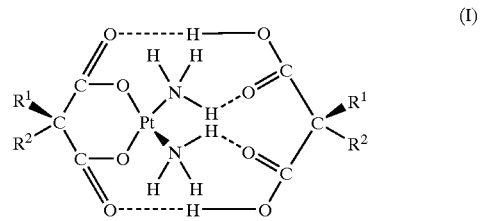

wherein
$R^1$ and $R^2$ are same or different, and independently represent hydrogen, a $C_1$–$C_{12}$-alkyl group, halogen, an amino group, a cyanide group, a hydroxyl group, an acyl group, a phosphoryl group or a phosphoamido group;
or represent a saturated or unsaturated 3–12-element carbocycle, which is formed by interlinking $R^1$ and $R^2$ together with the carbon atoms, that $R^1$ and $R^2$ are attached to;

said process comprises:
1) reacting substances of the genus of carboplatin or carboplatin with dicarboxylic acid ligand derivatives of formula (III)

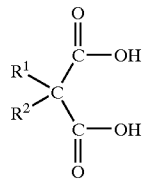

(III)

2) wherein $R^1$ and $R^2$ have the meanings defined in formula (I), to produce the derivative of double dicarboxylic acid diaminoplatin complex of formula (I); or reacting the dihalogen diaminoplatin having following formula $(NH_3)_2PtX_2$ wherein X is Cl or I, with silver nitrate or silver sulfate in water, to produce hydrated diaminoplatin nitrate of the formula $(NH_3)_2Pt(H_2O)_2(NO_3)_2$ or hydrated diaminoplatin sulfate of the formula $(NH_3)_2Pt(H_2O)_2SO_4$; and then reacting thus produced $(NH_3)_2Pt(H_2O)_2(NO_3)_2$ or $(NH_3)_2Pt(H_2O)_2SO_4$ with dicarboxylic acid ligand derivatives of formula (III) or their sodium salts or barium salts,

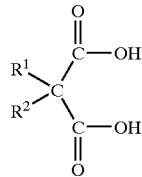

(III)

wherein the $R^1$ and $R^2$ have the meanings defined in abovementioned formula (I), to produce double dicarboxylic acid diaminoplatin complex of formula (I).

According to the above processes of present invention for preparing double dicarboxylic acid diaminoplatin of formula (I), every preparation step can be proceed at temperatures within relatively wide range, usually from 0° C. to 100° C., preferably from 10° C. to 50° C. time of every step is generally 2 to 16 hours.

According to the aforementioned processes of the present invention for preparing double dicarboxylic acid diaminoplatin in formula (I), the reactions are usually carried out under normal pressure. However, the reactions are also can be proceeded under increased pressure or decreased pressure, that is the reactions are usually proceeded under pressure from 0.1 bar to 10 bars.

According to the above processes of the present invention for preparing dicarboxylic acid diaminoplatin of formula (I), isomolar of starting raw materials are often used. However, it is allowable that one of the raw materials is relatively excessive to other raw materials.

The raw materials, i.e. dihalogen diaminoplatin and dicarboxylic acid ligand derivatives, are all known substances and can be prepared by known processes.

Furthermore, present invention also relates to an antitumor pharmaceutical composition, characterized in that, this composition comprises at least one kind of derivatives of dicarboxylic acid diaminoplatin complex of formula (I) at concentration of 0.1–0.5 wt % as an active component and balance of pharmaceutical acceptable carriers.

According to the pharmaceutical composition of the invention, it is preferred that the derivatives of dicarboxylic acid diaminoplatin complex of formula (I) as active component are those derivatives, that have a saturated 3–6-element carbocycle formed in formula (I) by interlinking $R^1$, $R^2$ and carbon atoms attached to them; more preferably it is double 1,1-cyclopropane dicarboxylic acid diaminoplatin complex or double 1,1-cyclobutane dicarboxylic acid diaminoplatin complex; most preferably it is double 1,1-cyclobutane dicarboxylic acid diaminoplatin complex.

The process for preparing the antitumor pharmaceutical composition of the invention is fairly simple, which is completed only by mixing the derivative of double dicarboxylic acid diaminoplatin complex of formula (I) and pharmaceutical acceptable carriers. This composition can be administered in the form of injection or capsule.

According to the invention, the pharmaceutical acceptable carriers can be selected from pure water, medical starch and vitamin C. The pharmaceutical composition can be made into injection with pure water, which can be administered subcutaneously, abdominally or intravenously. In addition, the pharmaceutical composition can also be made into oral capsule with medical starch and vitamin C.

The $LD_{50}$ of the pharmaceutical composition of the invention is tested as follows, for example:

283 mg/kg when bicycloplatin is administered abdominally;

50.46±0.93 mg/kg when bicycloplatin is administered intravenously;

500 mg/kg when bicycloplatin is taken orally;

180 mg/kg when double 1,1-cyclopropane dicarboxylic acid diaminoplatin is injected.

Generally speaking, the dosage of the pharmaceutical composition of the invention is one half of its $LD_{50}$.

Furthermore, the invention relates to the application of the derivative of double dicarboxylic acid diaminoplatin complex of said formula (I) in preparing antitumor drugs.

Many acute toxicity experiments, drug effect experiments and clinical trials lasting several years have been conducted with double dicarboxylic acid diaminoplatin complex described in formula (I) such as double 1,1-cyclobutane dicarboxylic acid diaminoplatin complex in formula (II). The results are as follows:

Acute toxicity dose limiting experiments in nude mice through intravenous, abdominal and oral administration showed low toxicity of the drug, with $LD_{50}$ of 50.46±0.93 mg/kg when administered intravenously, 283 mg/kg when administered abdominally and 500 mg/kg when taken orally.

The drug effect experiments relevant to therapeutic function of bicycloplatin were done in Cancer Hospital, Cancer Institute of Chinese Academy of Medical Sciences. The $IC_{50}$ for human hepatic cancer cells BEL-7402 was 1.3 μg/ml, which meant 1.3 μg/ml of bicycloplatin was needed to kill half of the cancer cells. In human breast cancer $IC_{50}$ was 2.8 μg/ml. Bicycloplatin was injected abdominally into nude mice bearing human breast cancer, lung cancer, hepatic cancer, colorectal cancer and ovary cancer to perform nude mice inoculation carcinostatic rate experiments. The mice were divided into three groups, which were given large dose ($LD_{50}×⅕$), middle dose ($LD_{50}×1/10$) and small dose ($LD_{50}×1/20$) respectively. The response carcinostatic rates were 90%, 95% and 70% respectively. The same doses given by stomach lavage led to a little lower carcinostatic rates. Beijing's institute for drug control carried out human hepatic cancer $H_{22}$ nude mice inoculation carcinostatic rate experiments.

Bicycloplatin was injected intravenously into mice divided into groups of large dose ($LD_{50} \times 1/5$), middle dose ($LD_{50} \times 1/10$) and small dose ($LD_{50} \times 1/20$) in contrast with cyclophosphamide. Every group was given 0.2 ml every time per day for seven consecutive days. The mice were put to death thirty days after inoculation. The response carcinostatic rates were 50.85%, 57.40% and 35.20% respectively for large dose group, middle dose group and small dose group. The nude mice had a normal life and normal diet. No death of nude mice was observed in every group containing ten mice. The inhibition rate reached 73.15% after two times of administration of the smallest dose of cyclophosphamide based on $LD_{50}$, but most of the mice were near death.

Rabbits were used in pharmacodynamic experiments of intravenously administered bicycloplatin while mice were used in those of orally given bicycloplatin. The assays of the content of platinum in animal serum at regular time showed that the concentration of the drug reached peak in 45 to 60 minutes and dropped to zero in 24 hours in blood.

To evaluate the safety of bicycloplatin, long-term toxicity experiments were carried out in which rats were given the drug continuously for three months. Thus we can not only know the target organs of toxic reactions and the reversibility of the damages through observing the main body reactions and degrees of injuries after three months of administration, but also determine nontoxic dose to provide reference for therapeutic safe dose.

The injuries of the drug to viscera are dose-dependent. Under the circumstances of therapeutic dose, the injuries become alleviated after one month of withdrawal. Small dose does a little damage to the group and the group can recover fully.

Carcinostatic Experiments in Vitro

1. The inhibition effect of bicycloplatin on the growth of human hepatic cancer BEL-7402 cells cultured in vitro was discovered via observing the dynamic growth of the treated cells. The result was as follows: on the second day there was still no significant difference between treated groups (with 10 μg/ml and 20 μg/ml respectively) and the control group. From the third day on, the survival cells in the treated group were less than that in the control group, in which the cells grew logarithmically while those in the treated group decreased gradually. The difference among the groups became wider as time went by; moreover, the survival cells of 20 μg/ml group were less than those of 10 μg/ml group. The results indicate bicycloplatin could inhibit the growth of human hepatic cancer BEL-7402 cells cultured in vitro dependent on time and dose (FIG. 4).

2. Within a certain range of doses, bicycloplatin can kill cancer cells selectively without damaging normal cells. The Academy of life sciences in Nanjing University carried out experiments in which human normal fibrous cells, epidermal cells and lung cancer cells, melanoma cells were treated with bicycloplatin equally, in which 50% of lung cancer cells and 80% of melanophore were killed while no injury occurred in human normal fibrous cells and epidermal cells (FIG. 5).

3. The influence of bicycloplatin on the ultra-microstructure of human hepatic cancer BEL-7402 cells was observed. After treated the BEL-7402 cells with different doses of bicycloplatin, the cells were pooled, fixed, embedded and sliced. Then the changes of the ultra-microstructure were observed via transmission electronic microscope. The results showed that the cells untreated appeared in the shape of irregular polygon, with abundant microvilli on the cell surface, plentiful organelles and different amount of glycogen granules in the plasma. In those treated cells there were degenerative changes of different degrees with the increase of the concentration of drug. The vacuoles and the lipid drop in the plasma increased drastically until necrotic changes, karyopyknosis, karyorrhexis, karyolysis and complete disintegration occurred (FIG. 6–FIG. 11).

It was found that double 1,1-cyclopropane dicarboxylic acid diaminoplatin complex was less soluble in water and more toxic in water than bicycloplatin in formula (II). But its antitumor effects were superior.

Next we illustrate the characteristics and advantages of the drugs in which active component is the derivative of double dicarboxylic acid diaminoplatin complex of formula (I) through a series of detailed experiments:

1. Determination of $IC_{50}$:

a). Cultured gastric cancer BGC-823 cells in RPMJ-1640 nutritional fluid containing 15% fetal calf serum; then inoculated them onto 96-well culture plate, $1 \times 10^4$ cells per well; Put it in an incubator with temperature of 37° C. and 5% of $CO_2$. Diluted 1% bicycloplatin water solution with RPMJ-1640 nutritional fluid containing 15% fetal calf serum, added them onto each well of the culture plate, three wells every concentration, and six wells left as blank control. After 72 hours of culture, added MTT fluid. An hour later, DMSO was added for coloration. OD value was assayed with enzyme labeling instrument. Finally, calculated the response rate of the drug in each concentration and determined $IC_{50}$ based on the coordinate process.

TABLE 2

| BGC-823 cells $IC_{50} = 14.80 \pm 1.34$ μg/ml | | | | | | | | | |
|---|---|---|---|---|---|---|---|---|---|
| Concentration (μg/ml) | 200 | 100 | 50 | 25 | 12.5 | 6.25 | 3.13 | 1.56 | 0.78 |
| Response rate (%) | 83.3 | 80.3 | 74.6 | 60.0 | 51.0 | 33.0 | 21.0 | 19.0 | 6.0 | b). Determination of $IC_{50}$ of bicycloplatin to kill human oral cancer KB cells using the same process as the experiment above.

TABLE 3

| KB cells $IC_{50} = 13.24 \pm 1.33$ μg/ml | | | | | | | | | |
|---|---|---|---|---|---|---|---|---|---|
| Concentration (μg/ml) | 200 | 100 | 50 | 25 | 12.5 | 6.25 | 3.13 | 1.56 | 0.78 |
| Response rate (%) | 93.3 | 93.0 | 77.1 | 66.6 | 36.7 | 26.2 | 28.2 | 14.8 | 5.9 |

2. Potent Antitumor Effects a). Divided 40 Kunming mice with weight ranging from 21 to 22 g, half male and half female randomly into 4 groups. Every group had 10 mice. Inoculated every mouse with 0.2 ml hepatic cancer $H_{22}$ cells subcutaneously in right abdomen. On the next day, inject 3 groups of mice abdominally with 30 mg/kg, 20 mg/kg, and 10 mg/kg of bicycloplatin respectively, one time per day for seven continuous days. The control group was given normal saline IP. The mice were put to death the day after withdrawal. Weighed the bodies and the tumor, calculated the carcinostatic rates. As shown in Table 4, the weight gain of the treated groups was less than that of the control group, no mortality occurs. The response rate was respectively 40.4%, 67.0% and 78.6% corresponding to 10 mg/kg, 20 mg/kg and 30 mg/kg of bicycloplatin administered.

TABLE 4

The carcinostatic rates of bicycloplatin on hepatic cancer $H_{22}$ cells

| Grade | Mice | | Body Weight (g) | | Tumor Weight (g) | Response Rate (%) | P Value |
|---|---|---|---|---|---|---|---|
| | Before Injection | After Injection | Before Injection | After Injection | | | |
| Control | 10 | 10 | 21.4 | 30.6 | 1.59 ± 0.48 | | |
| 30 mg/kg | 10 | 10 | 21.6 | 22.4 | 0.34 ± 0.09 | 78.6 | <0.001 |
| 20 mg/kg | 10 | 10 | 21.6 | 24.4 | 0.53 ± 0.26 | 67.0 | <0.001 |
| 10 mg/kg | 10 | 10 | 21.8 | 27.9 | 0.95 ± 0.29 | 40.4 | <0.01 | b). Table 5 showed the carcinostatic rates of bicycloplatin on carnuncle $S_{180}$ using the same method as the experiment above. It was indicated that bicycloplatin had potent antitumor effects on $S_{180}$ dependent on doses.

TABLE 5

The carcinostatic rates of bicycloplatin against carnuncle $S_{180}$

| Grade | Mice | | Body Weight (g) | | Tumor Weight (g) | Response Rate (%) | P Value |
|---|---|---|---|---|---|---|---|
| | Before Injection | After Injection | Before Injection | After Injection | | | |
| Control | 10 | 10 | 21.2 | 29.0 | 1.7 ± 0.57 | | |
| 30 mg/kg | 10 | 10 | 21.6 | 21.5 | 0.49 ± 0.16 | 71.0 | <0.001 |
| 20 mg/kg | 10 | 10 | 21.6 | 18.1 | 0.54 ± 0.16 | 68.0 | <0.001 |
| 10 mg/kg | 10 | 10 | 21.5 | 25.8 | 1.03 ± 0.30 | 39.7 | <0.01 | c). Treated human hepatic cancer BEL-7402 cells with 10 µg/ml, 20 µg/ml of bicycloplatin respectively. Then observed the dynamic growth of the cells for eight days. As shown in FIG. 4, in the first two days there was no significant difference between treated groups and the control group. From the third day on, the cells in the control group grew logarithmically while those in the treated group decreased gradually. The difference among the groups became wider as time went by. It indicated that bicycloplatin had potent antitumor effects on human hepatic cancer BEL-7402 cells dependent on doses.

3. Showed Slight Toxicity and Side Effects Only, and Selective Killing of Cancer Cells Without Damaging Normal Cells a). Divided 50 Kunming mice randomly into 5 groups, each having 10 mice, weighing from 18 g to 22 g and being half male and half female. Four groups were given bicycloplatin IP once a day for ten consecutive days in the concentrations of 400 mg/kg, 280 mg/kg, 196 mg/kg, 137 mg/kg, and 96 mg/kg respectively. Abnormal manifestations did not occur except local irritation of the high concentration. Death often happened on the 3rd to 7th day. $LD_{50} \pm SE = 210.5 \pm 1.14$ mg/kg based on Bliss method, which was significantly higher than the $LD_{50}$ of cisplatin and carboplatin determined under the same condition. The low toxicity of bicycloplatin was thus proved.

b). Chose two rabbits of similar age and weight (3.25 kg, 3.5 kg) and injected them intravenously with 100 mg of bicycloplatin respectively. At regular times we made blood sampling and determined the content of platinum in serum sample using atom absorption spectrum (AAS method). The data was shown in Table. 6. The concentration of the drug in blood soon reached peak injection, then decreased with time of 12 hours later, and the concentration became very low and dropped to zero at the time of 24 hours later. bicycloplatin can metabolize quickly in the body, so the toxicity and side effects were very slight.

TABLE 6

The content of platinum in rabbit's serum (µg/ml)

| Time (hr) | Rabbit 1 (3.25 kg) | Rabbit 2 (3.5 kg) |
|---|---|---|
| 0 | 34.6 | 58.0 |
| 0.5 | 20.5 | 21.8 |
| 1 | 10.4 | 20.3 |
| 2 | 6.2 | 10.8 |
| 4 | 2.4 | 4.2 |
| 6 | 1.9 | 2.8 |
| 8 | 1.7 | 2.3 |
| 10 | 1.6 | 2.1 |
| 12 | 0.9 | 2.2 |
| 24 | 0 | 0 | c). With $LD_{50}$ 500 mg/kg of oral acute toxicity experiments as reference, rats were administered orally $LD_{50}/10$ of bicycloplatin dissolved in 5% of glucose and 0.9% of sodium chloride, once a day for 90 consecutive days to observe long term toxicity. Weighed the rats once a week and adjusted doses according to weight changes. Stopped administration after 12 weeks and continued observing for 2 weeks. The results were as follows:

(1) No mortally occurred. There was no obvious abnormality of the diet, activity and state of the rats. Therefore, it was indicated that bicycloplatin had no adverse effect on rats.

(2) At the 12th week of administration and 2 weeks after withdrawal, the numbers of WBC and RBC, the content and classification of hemoglobin, and the number of platelet were determined through blood sampling from eyeball. They were all within normal ranges and there was no significant difference among the groups (p>0.05). There was also no significant difference (p>0.05) about blood urea nitrogen (BUN), glutamic-pyruvic transaminase (GPT), and glutamic-oxaloacetic transaminase (GOT) between the treated groups and the control group.

(3) The rats were put to death after observation. Visceral coefficients were determined. The weights of the livers of the treated groups were slightly heavier than that of the control group, but they were still within the normal range. The other visceral coefficients were all normal.

(4) The heart, liver, spleen, lung, kidney, stomach, duodenum, ovary gland, testis, prostate gland, suprarenal gland, thyroid gland of the rats were histologically examined. There were different degrees of hyperemia and edema in the livers and spleens of the treated groups. No organic changes caused by the drug are found in other visceras.

d). Treated human normal fibrous cells, epidermal cells and lung cancer cells, melanoma cells with bicycloplatin equally. The results were shown in FIG. 5. Within a certain range of doses, 50% of lung cancer cells and 80% of melanophore were killed while no injury occurred in human normal fibrous cells and epidermal cells. It showed that bicycloplatin could kill cancer cells selectively without damaging normal cells.

e). After treated with different doses of bicycloplatin, human hepatic cancer BEL-7402 cells were observed under transmission electronic microscope. The cells untreated appeared in the shape of irregular polygon, with abundant microvilli on the cell surface, plentiful organelles and different amount of glycogen granules in the plasma. In those treated cells there were degenerative changes of different degrees with the increase of the concentration of bicycloplatin. The vacuoles and the lipid drop in the plasma increased drastically until necrotic changes, karyopyknosis, karyorrhexis, karyolysis and complete disintegration occurred. Five days later cell death occurred.

Typical Cases Treated by Capsules Orally and Injections of the New Antitumor Drug of Bicycloplatin 1. The oral capsules were composed of bicycloplatin and adjuvant. The patients took the oral capsules containing 20–30 mg of bicycloplatin.

Cured Cases:

Patient Zhu, male, 64 years old, cystic cancer: One of his chief complains was hematuria. At first laser treatment were used. After three times of relapse, he began to take bicycloplatin. The three masses with size of 2×2 cm$^2$ disappeared completely. There were no abnormalities in the two kidneys and the cyst.

Patient Wang, female, 65 years old, late hepatic cancer, critically ill: Then she began to take bicycloplatin and was injected 30 mg of AT intravenously. After 45 days of administration, the tumor diminished from 4.7×3.1 cm to 2.3×1.7 cm. At last, the tumor disappeared. She was cured and returned to normal life.

2. Injections of bicycloplatin water solution at the concentration of 1% in 5 ml per ampoule. Bicycloplatin water solution was dissolved in 100 ml injection containing 5% of glucose and 0.9% of sodium chloride and injected intravenously once every two days, two ampoules every time. 100 ml of sodium chloride injection should be transfused after the dripping of bicycloplatin. A course of treatment took 6 times (12 ampoules). The second course of treatment began after an interval of two weeks. After three consecutive courses of treatment, general examination was taken.

Patient Ma, male, 83 years old, late recurrent hepatic cancer, 2×2 cm of lung metastatic carcinoma: Then he began to take bicycloplatin four times a day, 4–6 capsules every time. After two months, the lung metastatic carcinoma disappeared and the bone metastatic carcinoma diminished from 18×14 cm to 14×11 cm. The primary focus of hepatic cancer became lessened, with a smoother margin. During the treatment period he was also instilled injections of bicycloplatin once every two days, two ampoules every time. After a total of five courses of treatment, the patient had good mental state and appetite. His weight increased from 59 kg to 61 kg. Changes were little in hemogram.

Patient Xu, male, 59 years old, low differentiated squamous carcinoma of nasopharynx, recurrent ten years after radiotherapy, at late stage, metastasis to lymph tissue: Due to the compression of 8×8 cm mass on bronchus and esophagus when recurrent, he had difficulty in respiration and swallowing. Respiratory machine was needed through bronchial incision. He had had three times of cardiac arrest, the blood pressure decreased to 30/50 mmHg. Then he was injected injections of bicycloplatin once every two days, two ampoules every time. In 50 days, 50 ampoules were injected. After one week's break, the injection continued. In total, the dosage was 74 ampoules. The patient was on the mend day by day. At discharge, hemoglobin was 8.0 g, the number of WBC was 3000, and both were within normal range. The result of B-ultrasound showed masses of 15×10 mm$^2$, 9×8 mm$^2$ and 6×5 mm$^2$. Common reactions of antitumor drugs such as nausea and vomiting didn't occur before or after injection.

Patient Yang, male, 45 years old, melanoma, metastasis to liver and lung: After radiotherapy and chemotherapy were proved ineffective in Shanghai Cancer hospital, he was injected 36 ampoules of injections of bicycloplatin. The metastatic tumors had been cured and the melanoma had necrosed.

Patient Li, male, 49 years old, 3.3×3.3 cm of primary hepatic cancer, metastasis to left and right bile duct, with jaundice owing to cancer embolus in portal vein: He was injected 36 ampoules of injections of bicycloplatin for three courses of treatment. By the end of the 1st course of treatment, the tumor in the left hepatic lobe diminished to 3.3×3.3 cm. By the end of the 2nd course of treatment, the tumor basically disappeared, cancer embolus in portal vein also disappeared, and the right bile duct was only dilated to 0.8 cm. During the 3rd course of treatment, the patient's condition was stable. He had good mental state and appetite. Changes were little in hemogram. He once had periodic fever lasting about 10 hours. Sometimes he had periodic pain in the focus.

Patient Meng, male, 48 years old, adenocarcinoma of lung at late stage diagnosed by 301 hospital. After administration of injections of bicycloplatin intravenously and oral capsules, the symptoms such as coughing, asthma and sputum all disappeared. Now he was cured in general.

One foreign patient, male, 60 years old, intestinal cancer metastasis to liver accompanied with jaundice diagnosed by Russia, Cancer hospital of Chinese Academy of Medical Sciences and Air Force Hospital. He came to China for treatment upon the doctor's recommendation after having operation in Russia. After administration of 36 ampoules of injections of bicycloplatin intravenously and 36 oral capsules, the metastasis to liver disappeared. Now he was cured in general.

All of the scientific experiments such as in vitro experiments, clinical trials, acute toxicity experiments and long term toxicity experiments prove that derivatives of double dicarboxylic acid diaminoplatin complex of formula (I) (especially bicycloplatin and 1,1-cyclopropane dicarboxylic acid diaminoplatin complex) are a new generation of safe and effective antitumor drugs, which brings new hopes for cancer therapy of human.

Figure 1:
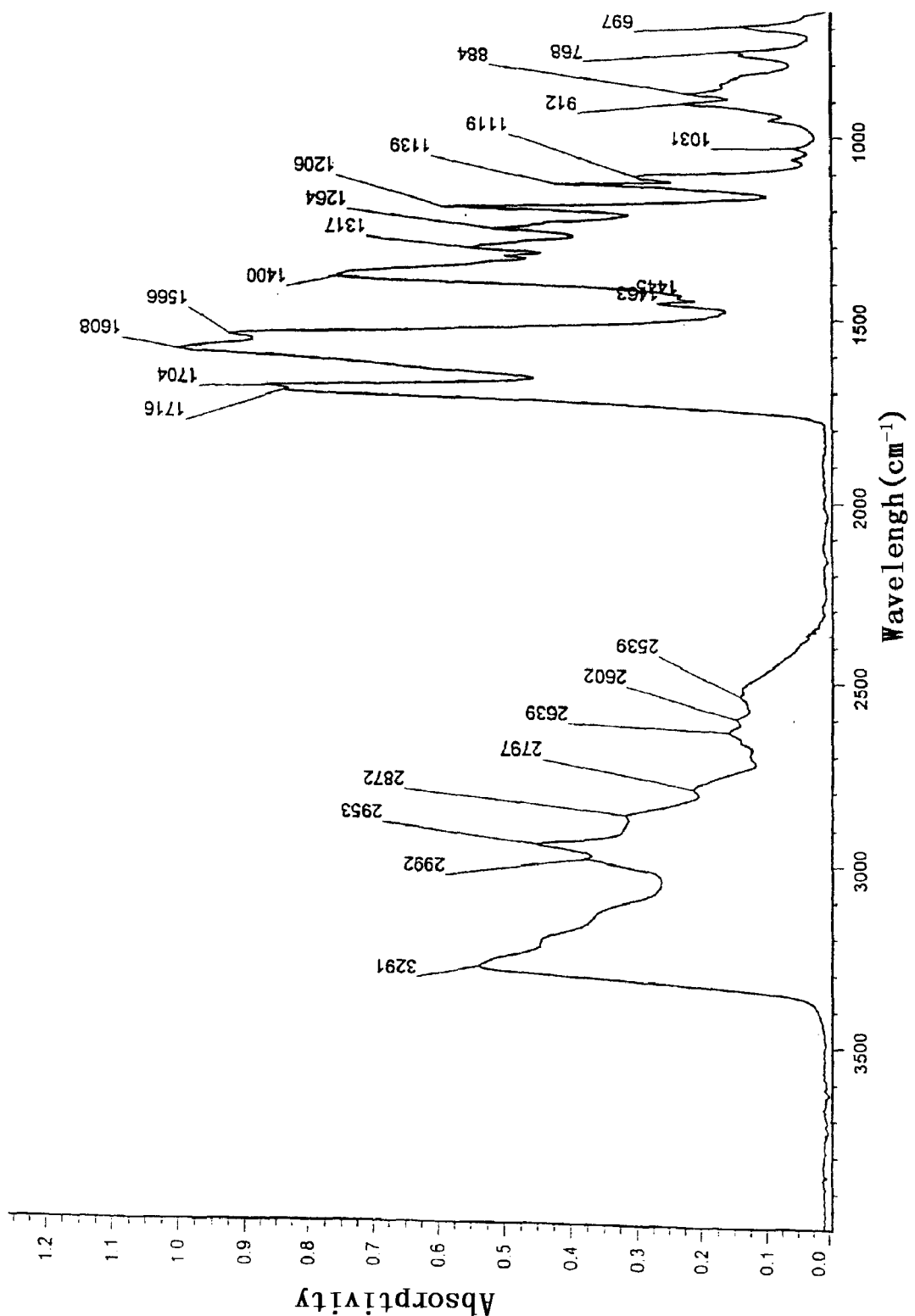
FIG. 1 shows infrared spectrum of bicycloplatin.

The illustration and attribution of the main peaks in FIG. 1 are listed as follows:

The peak of 3291 cm$^{-1}$ is the stretching vibration peak of Pt←–NH$_3$;

The slowly rising peak of 2539–2992 cm$^{-1}$ indicates that there exists no —COO$^-$ group of carboxylate, but exists —COOH group of carboxylic acid in bicycloplatin.

The strong peaks of 1716 cm$^{-1}$ and 1704 cm$^{-1}$ are stretching vibration peaks of —C═O of carboxylic acid group in bicycloplatin.

The strong peaks of 1608 cm$^{-1}$ and 1566 cm$^{-1}$ are stretching vibration peaks of —C═O of —COO—Pt in the molecule.

The strong absorption peak of 1400 cm$^{-1}$ is the variable angular vibration absorption peak of —C═O.

The illustration of the peaks of 697–1317 cm$^{-1}$ in fingerprint region is omitted.

The infrared spectrometry data above is the fingerprint sign to double 1,1-cyclobutane dicarboxylic acid diaminoplatin complex(II).

Figure 2A:
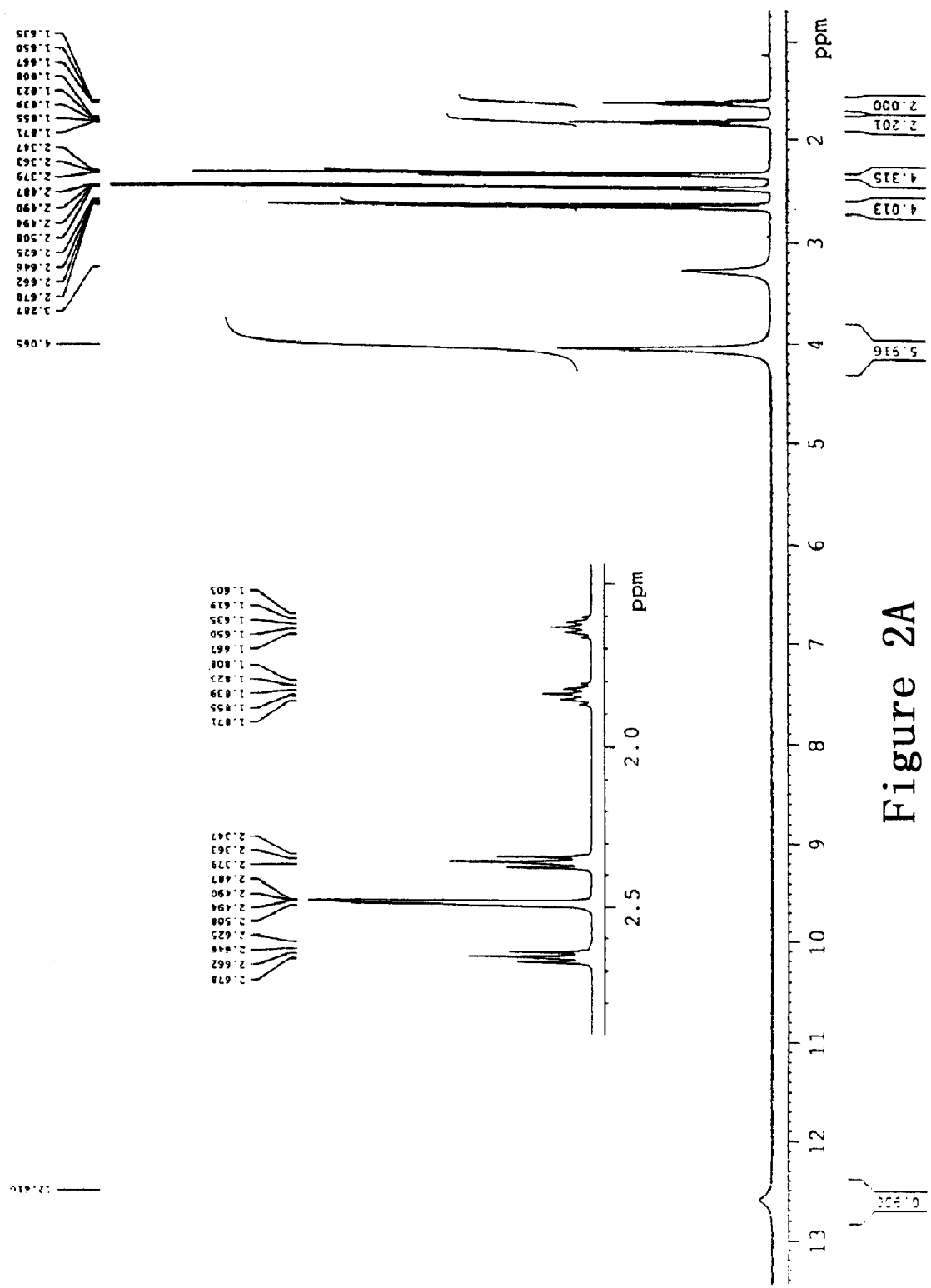
FIG. 2A shows $^1$H-NMR spectrum of bicycloplatin.

The illustration of $^1$H-NMR spectrometry in FIG. 2A is as follows:

| δ (ppm) | Peak shape | JHz | Numbers of H | Explanation of Proton Groups |
|---|---|---|---|---|
| 1.64 | quintet | 7.5 | 2 | two magnetic equal H of the 3rd CH$_2$ of the right tetratomic ring of formula (II) |
| 1.84 | quintet | 7.5 | 2 | two magnetic equal H of the 3rd CH$_2$ of the left tetratomic ring of formula (II) |
| 2.36 | triplet | 7.5 | 4 | four magnetic equal H of the 2nd and 4th CH$_2$ of the right tetratomic ring of formula (II) |
| 2.49 | multiplet | — | — | H unoxidized in solvent DMSO |
| 2.65 | triplet | 7.5 | 4 | four magnetic equal H of the 2nd and 4th CH$_2$ of the right tetratomic ring of formula (II) |
| 3.28 | singlet | — | — | trace H$_2$O in solvent of DMSO |
| 4.06 | singlet | — | 6 | six magnetic equal H of the two NH$_3$ of Pt of formula (II) |
| 12.61 | singlet | — | 2* | two magnetic equal H of the two —COOH of formula (II) |

The data above is in complete accordance with the structure of bicycloplatin displayed by formula (II).

The molecular weight of bicycloplatin is 515.36.

Figure 2B:
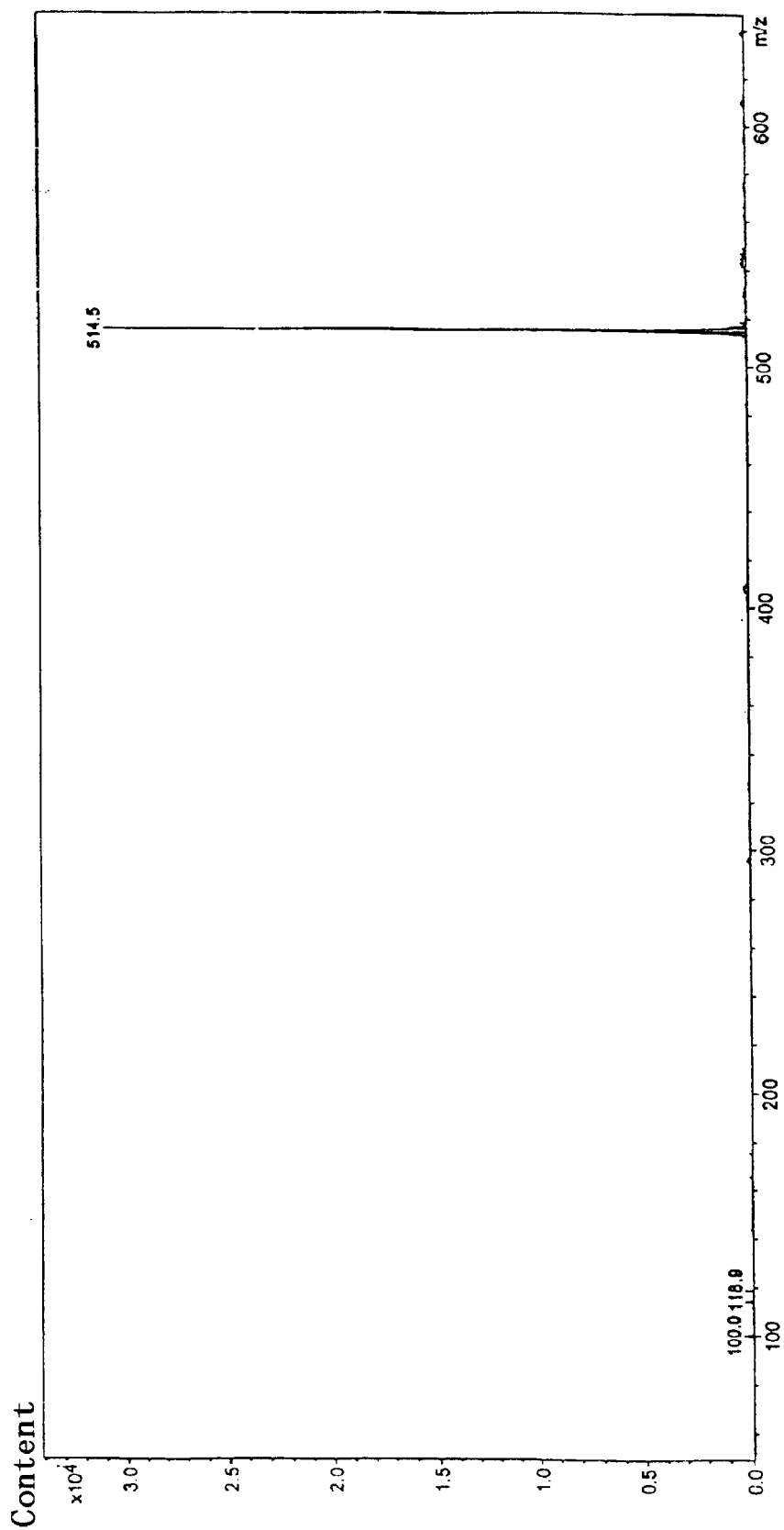
FIGS. 2B and 2C shows anion ESI-MS of bicycloplatin.

M–1 quasimolecule ion peak m/$_2$ 514 is clearly shown in FIG. 2B.

Figure 2C:
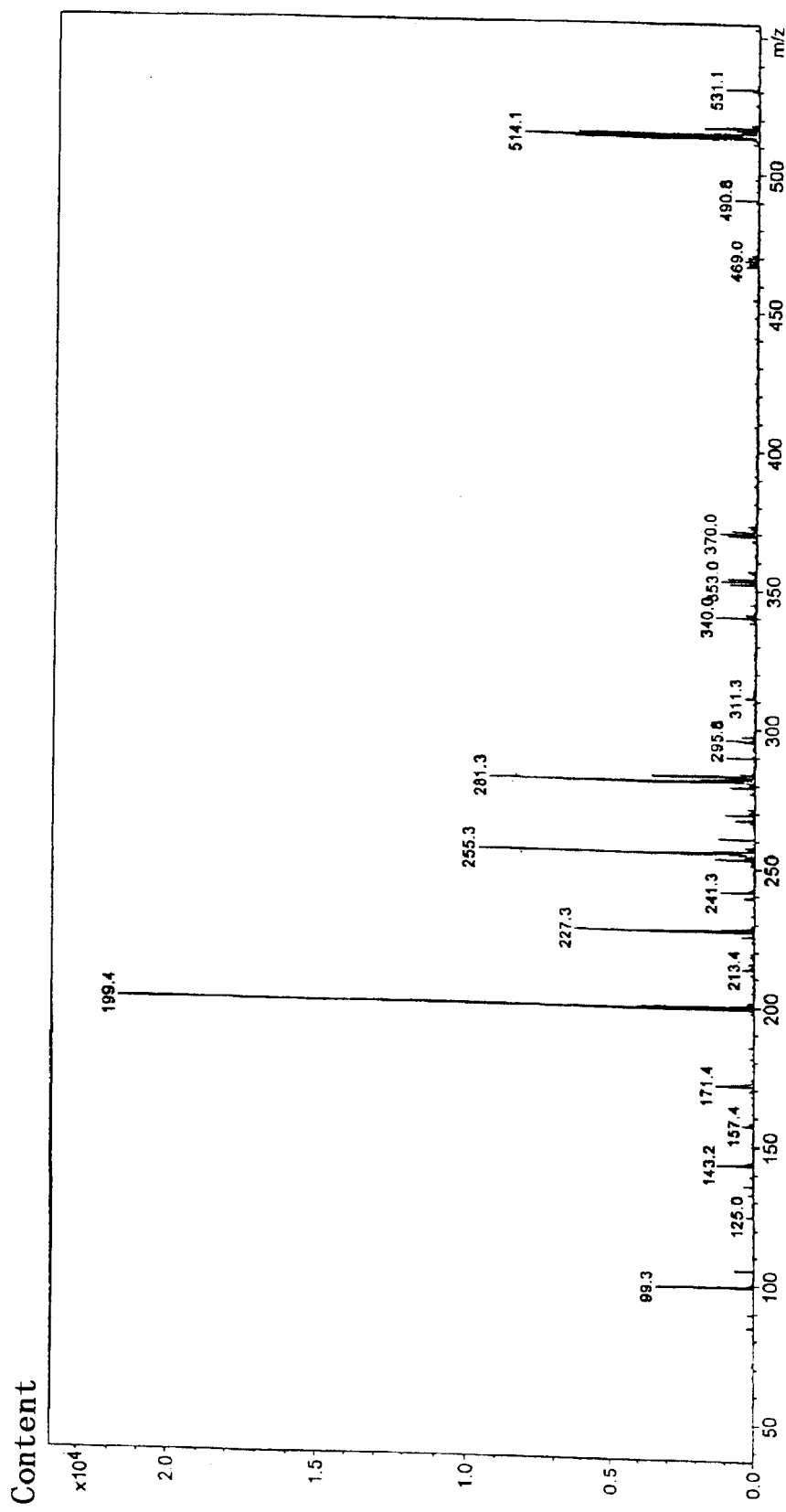

In FIG. 2C, fragments represented by all peaks are reasonable according to the structure of organic compounds.

Figure 4:
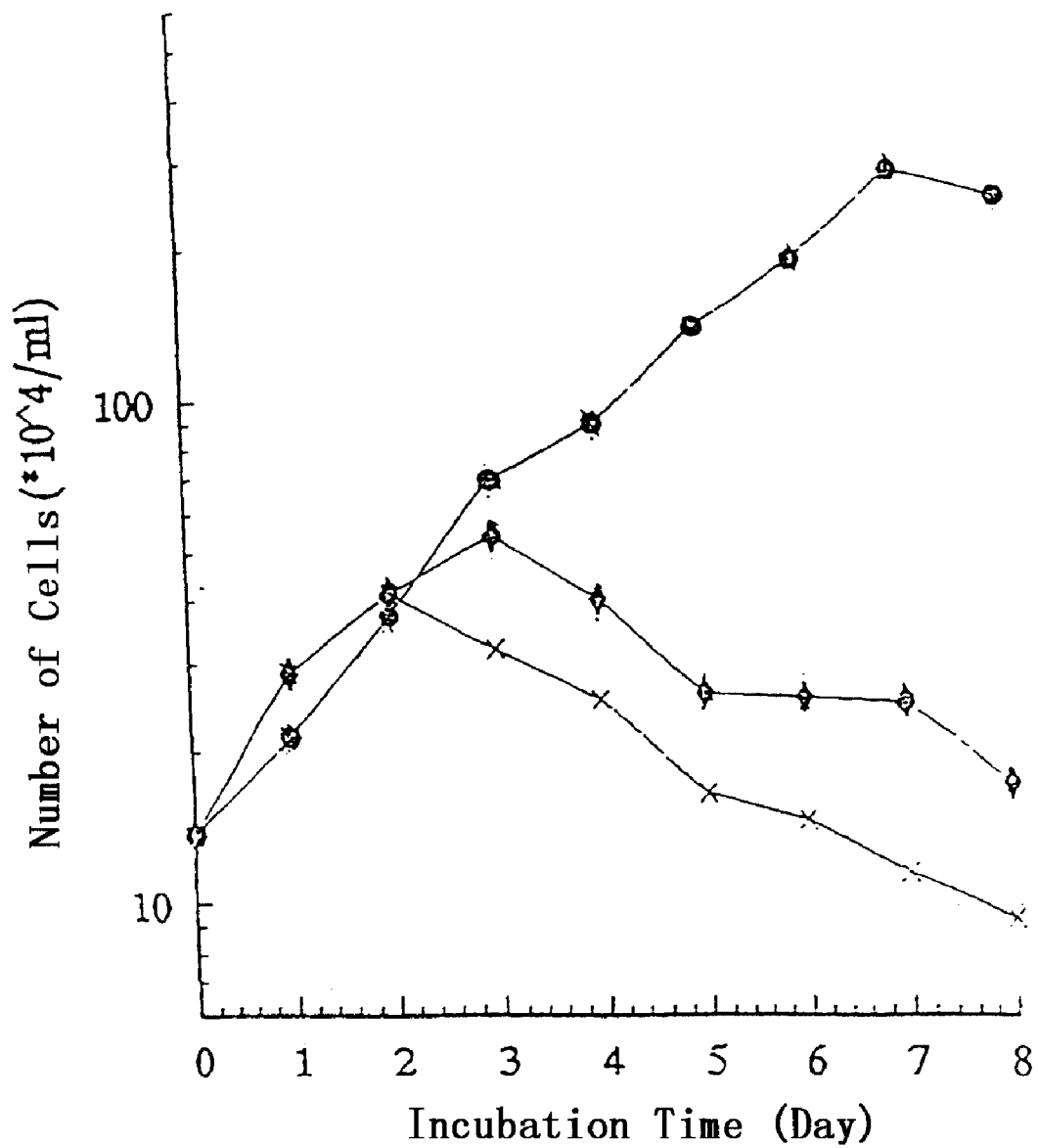
FIG. 4 is the growth curve of human hepatic cancer BEL-7402 cells treated by bicycloplatin.

In FIG. 4, "●" represents the control group; "♦" represents the 10 μg/ml group, "X" represents the 20 μg/ml group.

Figure 5:
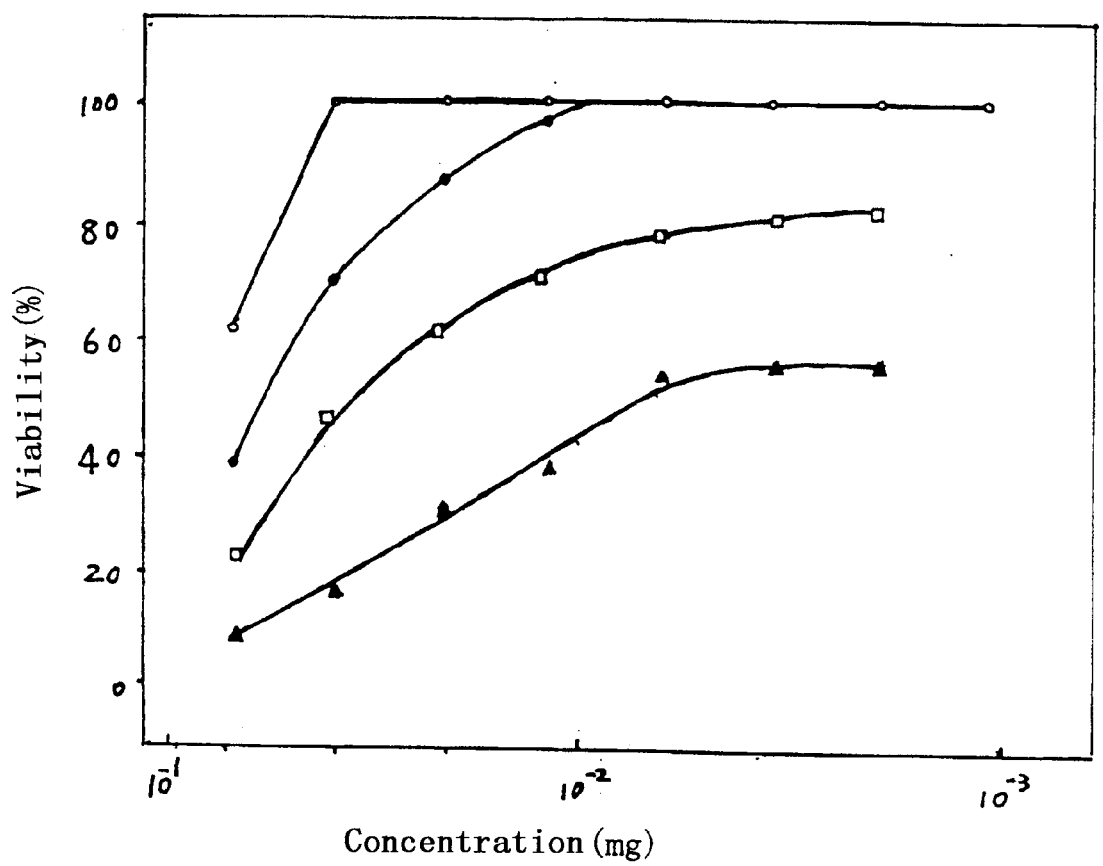
FIG. 5 is the curve of bicycloplatin selectively killing cancer cells.
Figure 6:
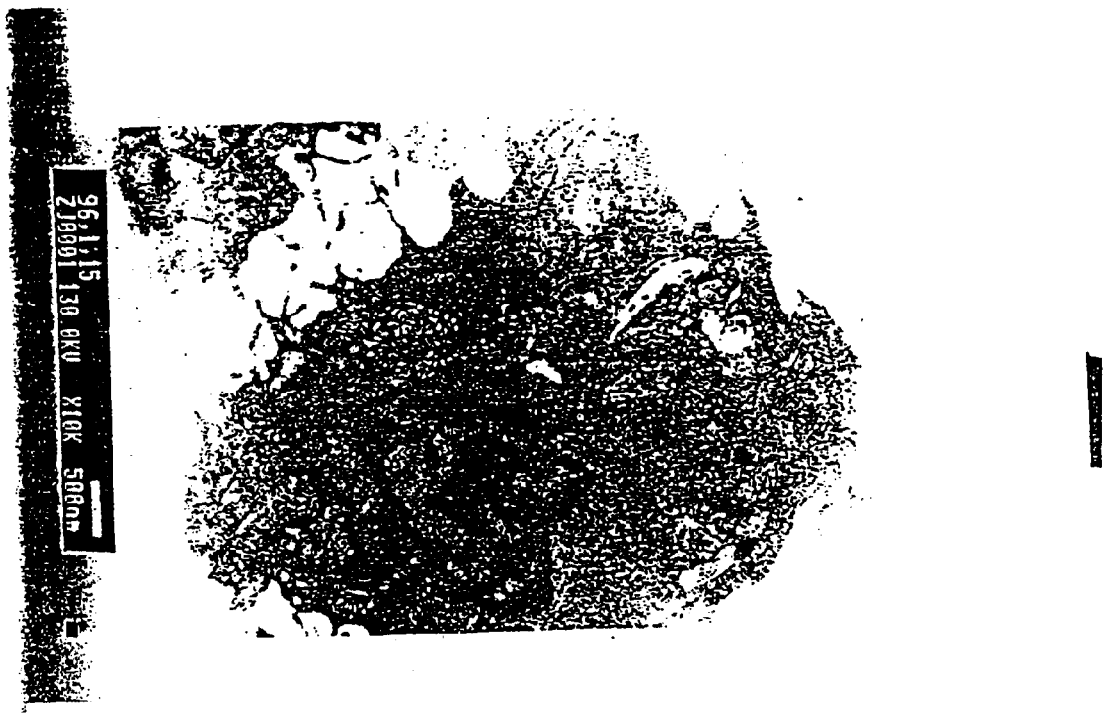
FIG. 6 is the blank control of BEL-7402 cells (EM× 10000).
Figure 7:
FIG. 7 is the blank control of BEL-7402 cells (EM×6000).
Figure 8:
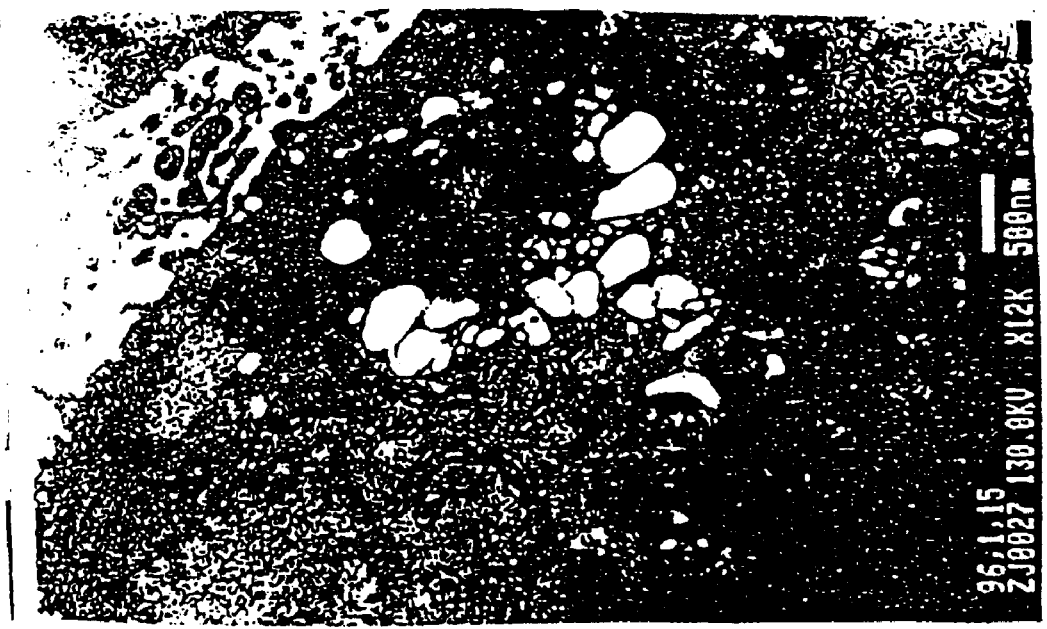
FIG. 8 is the vacuole degeneration of BEL-7402 cells (EM×12000).
Figure 9:
FIG. 9 is the of BEL-7402 cells (EM×12000).
Figure 10:
FIG. 10 shows karyorrhexis of BEL-7402 cells (EM× 6000).
Figure 11:
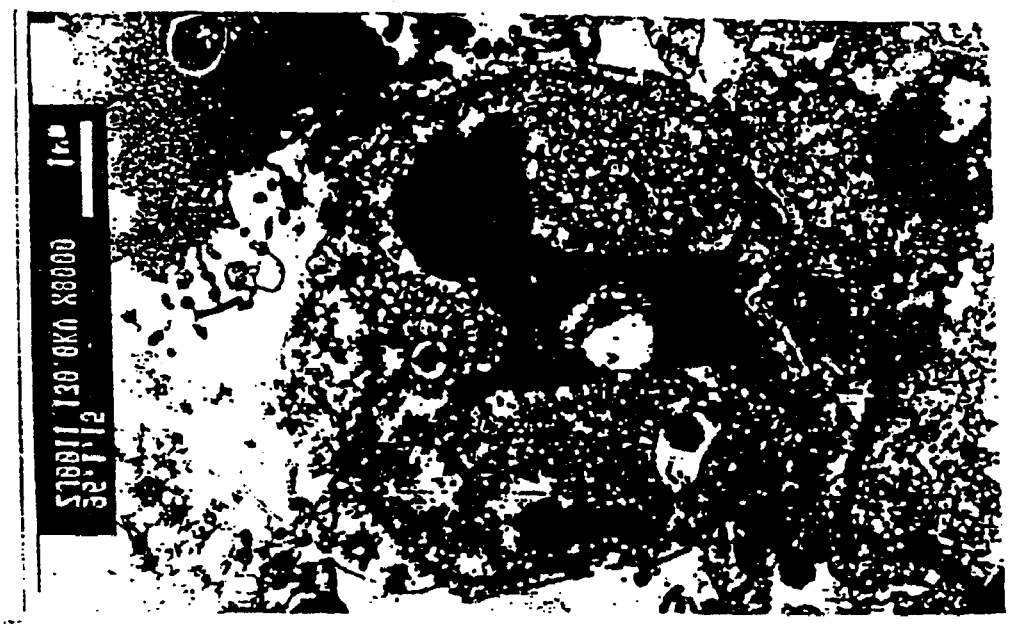
FIG. 11 shows karyorrhexis of BEL-7402 cells (EM× 8000).

In FIG. 5 "○" represents normal human fibrous cells; "●" represents normal human epidermal cells; "▼" represents human melanoma cells; "□" represents human hepatic carcinoma cells.

Incorporated with the following examples of preparing derivatives of formula (I) and the pharmaceutical compositions thereof, the invention shall be further described in detail.

EXAMPLE 1

The Preparation of Double 1,1-Cyclobutane Dicarboxylic Acid Diaminoplatin Complex Put 3.54 g (10.0 mmol) of carboplatin and 200 ml of pure water into a reaction flask, and stirred them while keeping away from light until the carboplatin was completely dissolved. While stirring, added 16.2 g (10.0 mmol) of cyclobutane dicarboxylic acid into the reaction flask in batches. kept stirring until it was completely dissolved to form a mixture. Next dried the mixture by rotating evaporation to get a dried product. Then added 50 ml of ethanol into the dried product, agitated for 2 hours to cause a precipitate and filtrated it out. The precipitate was washed with 10 ml×3 ethanol, and then recrystallized from distilled water, evacuated and dried naturally to yield the title compound.

EXAMPLE 2

The Preparation of Double 1,1-Cyclopropane Dicarboxylic Acid Diaminoplatin Complex Put 6.5 g (20.8 mmol) of Ag$_2$SO$_4$ and 100 ml of pure water in a reaction flask and then stirred them while keeping away from light until Ag$_2$SO$_4$ was completely dissolved. While stirring, added in 6.2 g (20.7 mmol) of Cis-(NH$_3$)$_2$PtCl$_2$ into the reaction flask in batches. After the addition of Cis-(NH$_3$)$_2$PtCl$_2$ was finished, a reaction was taken place in the reaction flask under stirring for 5 hours in water bath at 40° C. and then filtrated the reaction mixture while it was still warm, and washed with 10 ml×3 warm water. The filtrate was then transferred into another reaction flask and 20 ml (232.6 mmol) of 35%H$_2$O$_2$ was added in batches. The mixture was stirred for 4 hours at room temperature, then heated to 60° C. and maintained at this temperature for 2 hours. 12.0 g (25.0 mmol) of barium cyclomalonate was added into the reaction product and stirred them at 60° C. for 8 hours, then filtered while still warm and washed with 10 ml×3 warm water. The filtrate was then transferred into another reaction flask and dried by rotating evaporation.

Then added 50 ml of ethanol into the dried product and filtrated it after 2 hours of agitation to get a precipitate. The precipitate was washed with 10 ml×3 ethanol, and then recrystallized from distilled water, evacuated and dried naturally to yield the title compound. The resulting compound was decomposed at 220° C.

EXAMPLE 3

The Preparation of Double 1,1-Cyclobutane Dicarboxylic Acid Diaminoplatin Complex Put 10.5 g (61.8 mmol) of $AgNO_3$ and 100 ml of pure water in a reaction flask, and then stirred them until $AgNO_3$ was completely dissolved. While stirring, added 9.3 g (31.1 mmol) of dichlorodiaminoplatin into the reaction flask in batches. After finishing adding the dichlorodiaminoplatin, a reaction was taken place in the reaction flask under stirring for 5 hours below 40° C. and then filtrated the reaction mixture while it was still warm, and washed with 10 ml×3 warm water. The filtrate was then transferred into the reaction flask and 30 ml (349.0 mmol) of 35%$H_2O_2$ was added in batches (15 ml+15 ml×3). The mixture was stirred for five hours at room temperature, then heated to 60° C. and maintained at this temperature for two hours. 12.0 g (69.0 mmol) of cyclosuccinic acid was added into the reaction product and stirred them at 60° C. for eight hours, then filtered while still warm and washed with 10 ml×3 warm water. The filtrate was then transferred into the reaction flask and dried by rotating evaporation. Then added 50 ml of ethanol into the dried product, filtrated it after two hours of agitation to get a precipitate. The precipitate was washed with 10 ml×3 ethanol, and then recrystallized with distilled water, evacuated and dried naturally to yield the title compound.

EXAMPLE 4

The Preparation of Double 1,1-Cyclobutane Dicarboxylic Acid Diaminoplatin Complex The title compound was prepared by the same steps as described in Example 3, in which 15.0 g of diiododiaminoplatin was used to substitute the 9.3 g of dichlorodiaminoplatin in Example 3.

EXAMPLE 5

The Preparation of Double 1,1-Cyclopentane Dicarboxylic Acid Diaminoplatin Complex Put 10.5 g (61.8 mmol) of $AgNO_3$ and 100 ml of pure water in a reaction flask, and then stirred them until $AgNO_3$ was completely dissolved. While stirring, added 9.3 g (31.1 mmol) of dichlorodiaminoplatin into the reaction flask in batches. After finishing adding the dichlorodiaminoplatin, a reaction was taken place in the reaction flask under stirring for 5 hours below 40° C. and then filtrated the reaction mixture while it was still warm, and washed with 10 ml×3 warm water. The filtrate was then transferred into the reaction flask and 30 ml (349.0 mmol) of 35% $H_2O_2$ was added in batches (15 ml+15 ml×3). The mixture was stirred for five hours at room temperature, then heated to 60° C. and maintained at this temperature for 2 hours. 15.6 g (53.0 mmol) of barium salt of cyclopentanedioic acid was added into the reaction product and stirred them at 60° C. for eight hours, then filtered while still warm and washed with 10 ml×3 warm water. The filtrate was then transferred into the reaction flask and dried by rotating evaporation. Then added 50 ml of ethanol into the dried product, filtrated it after 2 hours of agitation to get a precipitate. The precipitate was washed with 10 ml×3 ethanol, and then recrystallized with distilled water, evacuated and dried naturally to yield the title compound.

EXAMPLE 6

The Preparation of Double 1,1-Cyclohexatane Dicarboxylic Acid Diaminoplatin Complex Put 6.7 g (39.4 mmol) of $AgNO_3$ and 100 ml of pure water in a reaction flask, and then stirred them until $AgNO_3$ was completely dissolved. While stirring, added 6.2 g (19.6 mmol) of dichlorodiaminoplatin into the reaction flask in batches. After finishing adding the dichlorodiaminoplatin, a reaction was taken place in the reaction flask under stirring for five hours below 40° C. and then filtrated the reaction mixture while it was still warm, and washed with 10 ml×3 warm water. The filtrate was then transferred into the reaction flask and 20 ml (232.6 mmol) of 35%$H_2O_2$ was added in batches. The mixture was stirred for five hours at room temperature, then heated to 60° C. and maintained at this temperature for two hours. 3.7 g (21.5 mmol) of cyclohexanedioic acid was added into the reaction product and then 1 ml (10.3 mmol) of hydrazine hydrate was dropped slowly within two hours while stirring at 45° C. The mixture was reacted for six hours. The reaction product was dried by rotating evaporation and then by evacuation for five hours. Then added 50 ml of methanol into the dried product and stirred them for 2 hours, filtrated them to get a precipitate. The precipitate was washed with 10 ml×3 methanol, and then recrystallized with distilled water, evacuated and dried naturally to yield the title compound.

EXAMPLE 7

The Preparation and Refinement of Double 1,1-Cyclobutane Dicarboxylic Acid Diaminoplatin Complex 12.4 g of dichlorodiaminoplatin was suspended in 800 ml of pure water, and then a chemically measured of 1N $AgNO_3$ aqueous solution was added while agitation away from light. The mixture was reacted for 4 hours at 40° C. Then the reaction product was put in the refrigerator to filtrate for removal of the precipitate (used for recovering). A stoichiometric amount of cyclobutane dicarboxylic acid was added into the filtrate and stirred for 16 hours at 60° C. The reaction product was decompression rotating evaporated until microcrystal appeared and then put in the refrigerator for 48 hours followed by filtration. The crystal was collected as crude product and refined by recrystallization from distilled water. The yield rate of refined product was 90%. Melting point: 182~184° C.

EXAMPLE 1 PHARMACEUTICAL PREPARATION: INJECTIONS 50 g of bicycloplatin was dissolved in 5000 ml of pure water. The mixture was filtrated by absorbing via 7.5 g of medical charcoal and then re-filtrated via 2 μm-filtration membrane for two times. The filtrate was distributed in 1000 ampoules of 5 ml and then the ampoules were sealed via burning.

EXAMPLE 2 OF PHARMACEUTICAL PREPARATION: ORAL DRUGS 24 g of bicycloplatin, 1600 g of medical starch and 120 g of Vitamin C was mixed and ground in the stirrer, and then sterilized. The powder was distributed into 5000 capsules.

Figure 3:
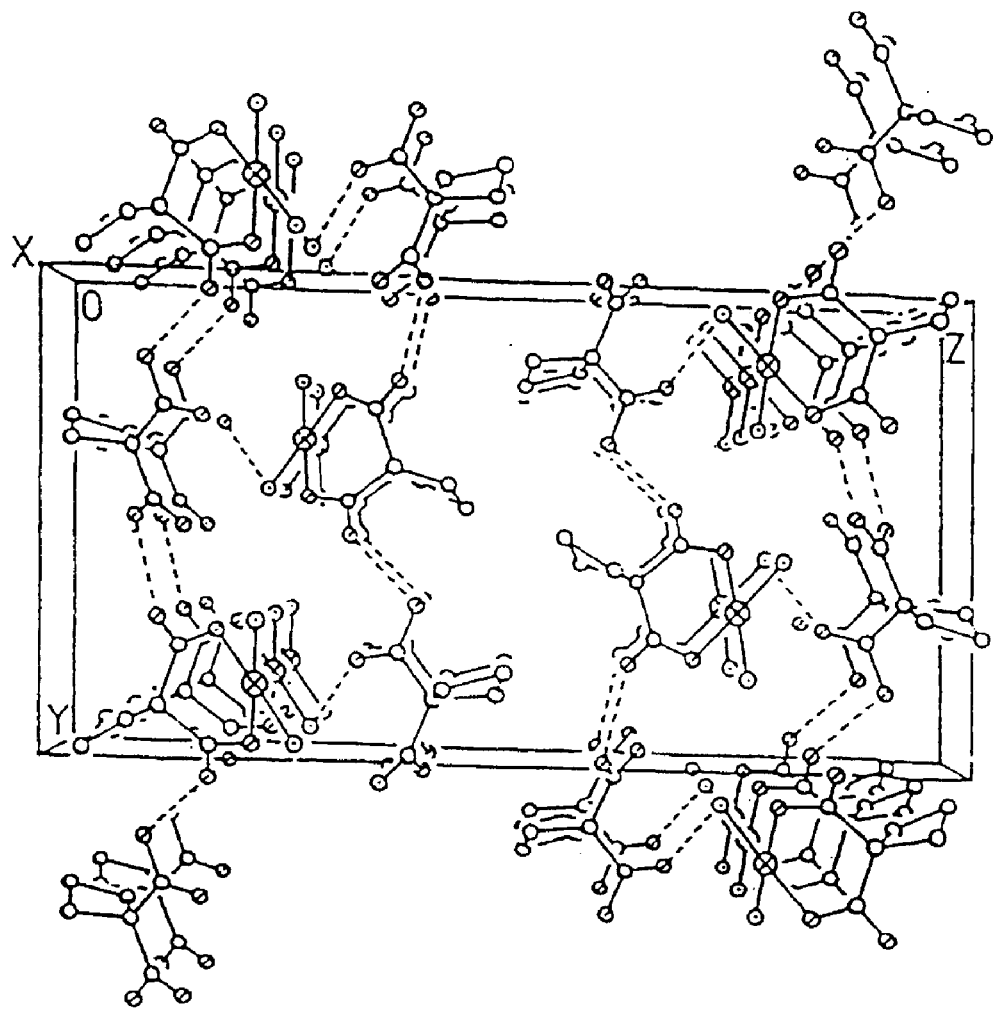
FIG. 3 shows X-ray diffraction unit cell stacking of bicycloplatin.

The aforementioned bicycloplatin of formula (II) prepared according to Example 1, 3, 4 and 7 was colorless needle crystal. The colorless needle crystal was made into white micro-crystal powder by applying micelle. The structure, constitution and purity of bicycloplatin of formula (II) was fully determined by many modem physical and chemical methods such as measurement of melting point, solubility and pH, trace element analysis for C, H and N, analysis of the content of platinum by ICP-EAS method, differential thermal analysis, thermo-gravimetric analysis, infrared spectrum, UV spectrum, laser Lamen spectrum, thin layer chromatograph (TLC), $^1$H, $^{13}$C, $^{195}$Pt-NMR, X-ray four circle diffraction, etc. The data of IR, $^{13}$C-NMR, TLC and X-ray singular crystal structure analysis showed that 1,1-cyclobutane dicarboxylic acid diaminoplatin was a new compound with a cage structure. The results of Infrared spectrum, $^1$H-NMR, MS and X-ray four circle diffraction were shown in FIGS. 1–3 and the following table 1.

TABLE 1

| The result of X-ray four circle diffraction | |
|---|---|
| Size of singular crystal (mm) | 0.2 × 0.2 × 0.3 |
| Crystal system | Monoclinic system |
| Space group | P21/C |
| Cell parameter | a = 5.679(2)A |
| | b = 12.107(2)A |
| | c = 23.430(5)A |
| | β = 95.25(2)° |
| Volume | 1604.3(7)A$^3$ |
| Density | 2.123 mg/m$^3$ |
| Absorption coefficient | 8.876 mm$^{-1}$ |
| Lattice molecule number | 4 |

The new derivatives of double dicarboxylic acid diaminoplatin of formula (I) have surprising therapeutic effects against cancers, which have the following characteristics compared to the current antitumor platin analogous drugs:

A cage structure is formed by the four intramolecular H-bonds of the compound, in which the platinum atom is locked, so as to make the structure of the compound with certain stability. Therefore the attack of H$_2$O is weakened and the compound has considerable stability in water. The solubility in water is also improved and the toxicity is greatly reduced while the advantage of potent effect is retained. It can be administered subcutaneously, abdominally, intravenously and orally. We will use bicycloplatin in formula (II) as an example to illustrate the significant characteristics:

1. High Antitumor Activity

| IC$_{50}$ to cells of adenocarcinoma of breast: | carboplatin | 9.3 μg/ml |
| | bicycloplatin | 2.80 μg/ml |
| IC$_{50}$ to hepatic cancer cells BL7402 | carboplatin | 8.45 μg/ml |
| | bicycloplatin | 1.30 μg/ml |

2. Broad Antitumor Spectrum With Significant Therapeutic Effects to Genitourinary Cancer, Cephalocircular Cancer, Nasopharyngeal Cancer, Adenocarcinoma of Breast, Lung Cancer, Hepatic Cancer, Pancreatic Cancer, Gastric Cancer, Intestinal Cancer and Lymphatic Cancer, etc.

3. Low Toxicity

| LD$_{50}$ abdominal administration | Cisplatin | 13 mg/kg |
| | Carboplatin | 130 mg/kg |
| | Bicycloplatin | 283 mg/kg |
| Oral administration | Bicycloplatin | 500 mg/kg |
| | Carboplatin | ineffective |
| | Cisplatin | ineffective |

Toxic reactions in clinical trial are ranged from 0 degree to 1 degree (according to five-degree classification by WHO), no adverse reactions occur.

4. Good Solubility and Stability in Water

| Solubility in water (g/100 ml) | Cisplatin | 0.2 |
| | Carboplatin | 1.5 |
| | Bicycloplatin | 4.0 |

Cisplatin and carboplatin lose effectiveness in one day after dissolved in water while aqueous preparation prepared from bicycloplatin of formula (II) can be stored effective for a long period.

5. Effective Taken Orally

Derivatives of double dicarboxylic acid diaminoplatin are effective not only by injection, but also by taking orally. For example, capsules prepared from bicycloplatin of formula (II) and pharmaceutical acceptable excipient have significant therapeutic effects in a long period of clinical trials.

What we claim is:

1. A derivative of double dicarboxylic acid diaminoplatinum(II) complex, characterized in that, said derivative has the following general formula (I):

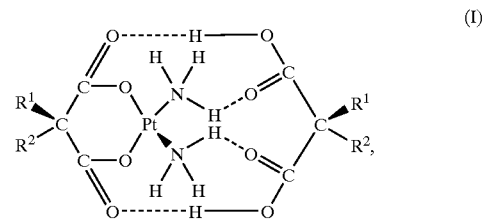

wherein
R$^1$ and R$^2$ are the same or different, and independently represent hydrogen, a C$_1$–C$_{12}$ alkyl group, halogen, an amino group, a cyanide group, a hydroxyl group, an acyl group, a phosphoryl group or a phosphoamido group; or
R$^1$ and R$^2$, taken together, represent a saturated or unsaturated 3-membered to 12-membered carbocyclic group.

2. The derivative of double dicarboxylic acid diaminoplatinum(II) complex according to claim 1, characterized in that, R$^1$ and R$^2$, taken together, represent a saturated 3-membered to 6-membered carbocyclic group.

3. The derivative of double dicarboxylic acid diaminoplatinum(II) complex according to claim 2, characterized in that, said derivative is double 1,1-cyclopropane dicarboxylic acid diaminoplatinum(II) complex or double 1,1-cyclobutane dicarboxylic acid diaminoplatinum(II) complex.

4. The derivative of double dicarboxylic acid diaminoplatinum(II) complex according to claim 3, characterized in that, said double 1,1-cyclobutane dicarboxylic acid diaminoplatinum(II) complex has the following formula (II):

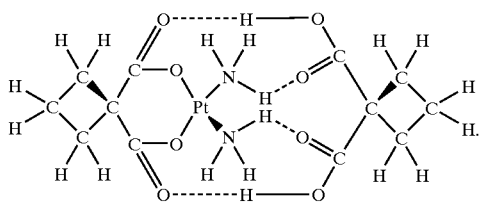

(II)

5. A process for preparing the derivative of double dicarboxylic acid diaminoplatinum(II) complex according to claim 1, characterized in that,
said process comprises reacting a substance of the class of carboplatin with dicarboxylic ligand derivatives of formula (III):

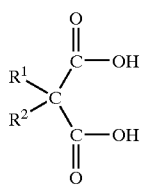

(III)

to produce the derivative of double dicarboxylic acid diaminoplatinum(II) complex of formula (I),
wherein $R^1$ and $R^2$ are the same or different, and independently represent hydrogen, a $C_1$–$C_{12}$ alkyl group, halogen, an amino group, a cyanide group, a hydroxyl group, an acyl group, a phosphoryl group or a phosphoamido group; or $R^1$ and $R^2$, taken together, represent a saturated or unsaturated 3-membered to 12-membered carbocyclic group.

6. An anti-tumor pharmaceutical composition, characterized in that, said composition contains 0.1–0.5 wt % of at least one derivative of double dicarboxylic acid diaminoplatinum(II) complex having formula (I) according to claim 1 and a pharmaceutical acceptable carriers.

7. The anti-tumor pharmaceutical composition according to claim 6, characterized in that, said derivatives of double dicarboxylic acid diaminoplatinum(II) complex of formula (I) are those in which $R^1$ and $R^2$, taken together, represent a saturated 3-membered to 6-membered carbocyclic group.

8. The anti-tumor pharmaceutical composition according to claim 7, characterized in that, said derivative of double dicarboxylic acid diaminoplatinum(II) complex of formula (I) is double 1,1-cyclopropane dicarboxylic acid diaminoplatinum(II) complex or double 1,1-cyclobutane dicarboxylic acid diaminoplatinum(II) complex.

9. The anti-tumor pharmaceutical composition according to claim 8, characterized in that, said derivative of double dicarboxylic acid diaminoplatinum(II) complex of formula (I) is double 1,1-cyclobutane dicarboxylic acid diaminoplatinum(II) complex.

10. The anti-tumor pharmaceutical composition according to any one of claim 6–9, characterized in that, said pharmaceutical composition is administrated in the form of injection or capsule.

11. A process for preparing the derivative of double dicarboxylic acid diaminoplatinum(II) complex according to claim 1, characterized in that, said process comprises the following steps:
(1) mixing dihalogen diaminoplatinum(II) with $AgNO_3$ or $Ag_2SO_4$, in water, then bringing them into reaction to produce $(NH_3)_2Pt(H_2O)_2(NO_3)_2$ or $(NH_3)_2Pt(H_2O)_2SO_4$, dihalogen diaminoplatinum(II) having a formula of $(NH_3)_2PtX_2$ wherein X is Cl or I; and
(2) reacting the produced $(NH_3)_2Pt(H_2O)_2(NO_3)_2$ or $(NH_3)_2Pt(H_2O)_2SO_4$ with dicarboxylic acid ligand derivatives of formula (III) or their sodium salts or barium salts, to produce double dicarboxylic acid diaminoplatinum(II) complex of formula I.

* * * * *